(12) United States Patent
Mudge et al.

(10) Patent No.: US 8,305,578 B1
(45) Date of Patent: Nov. 6, 2012

(54) IMAGING POLARIMETER

(75) Inventors: Jason D. Mudge, Los Altos, CA (US);
Miguel Virgen, Santa Clara, CA (US)

(73) Assignee: Lockheed Martin Corporation,
Bethesda, MD (US)

( * ) Notice: Subject to any disclaimer, the term of this patent is extended or adjusted under 35 U.S.C. 154(b) by 400 days.

(21) Appl. No.: 12/771,635

(22) Filed: Apr. 30, 2010

Related U.S. Application Data

(60) Provisional application No. 61/174,842, filed on May 1, 2009.

(51) Int. Cl.
*G01J 4/00* (2006.01)
(52) U.S. Cl. ........................................ 356/367
(58) Field of Classification Search ................... 356/364, 356/367
See application file for complete search history.

(56) References Cited

U.S. PATENT DOCUMENTS

| | | | | |
|---|---|---|---|---|
| 7,016,040 B2 * | 3/2006 | Chen et al. | ..................... | 356/364 |
| 2005/0062966 A1 * | 3/2005 | Chen et al. | ..................... | 356/364 |

OTHER PUBLICATIONS

Bruce D. Lucas, et al.; An Iterative Image Registration Technique with an Application to Stereo Vision; Computer Science Department, Carnegie-Mellon University, Pittsburg, PA; Apr. 1981; pp. 674-679.
J. Larry Pezzaniti, et al.; Four Camera Complete Stokes Imaging Polarimeter; Polarization: Measurement, Analysis, and Remote Sensing VIII; Proc. of SPIE vol. 6972, 69720J; 2008; pp. 1-12.
Jason Mudge, et al.; Near-infrared Simultaneous Stokes Imaging Polarimeter; Polarization Science and Remote Sensing IV; Proc. of SPIE vol. 7461, 74610L; Aug. 11, 2009; pp. 1-6.

* cited by examiner

*Primary Examiner* — Roy M Punnoose
(74) *Attorney, Agent, or Firm* — McDermott Will & Emery, LLP

(57) ABSTRACT

An imaging polarimeter and a method of utilizing the imaging polarimeter are provided. The method includes receiving a first light ray at a beam splitter and splitting the first light ray into second, third, fourth, and fifth light rays such that the second, third, fourth, and fifth light rays are simultaneously received on a flat focal plane. The method further includes outputting first, second, third, and fourth signals indicative of first, second, third, and fourth intensities, respectively, of the second, third, fourth, and fifth light rays, respectively, utilizing a sensor array disposed on the focal plane. The method further includes determining first, second, third, and fourth Stokes parameters for a pixel of the sensor array based on the first, second, third, and fourth signals, respectively, utilizing a computer.

24 Claims, 7 Drawing Sheets

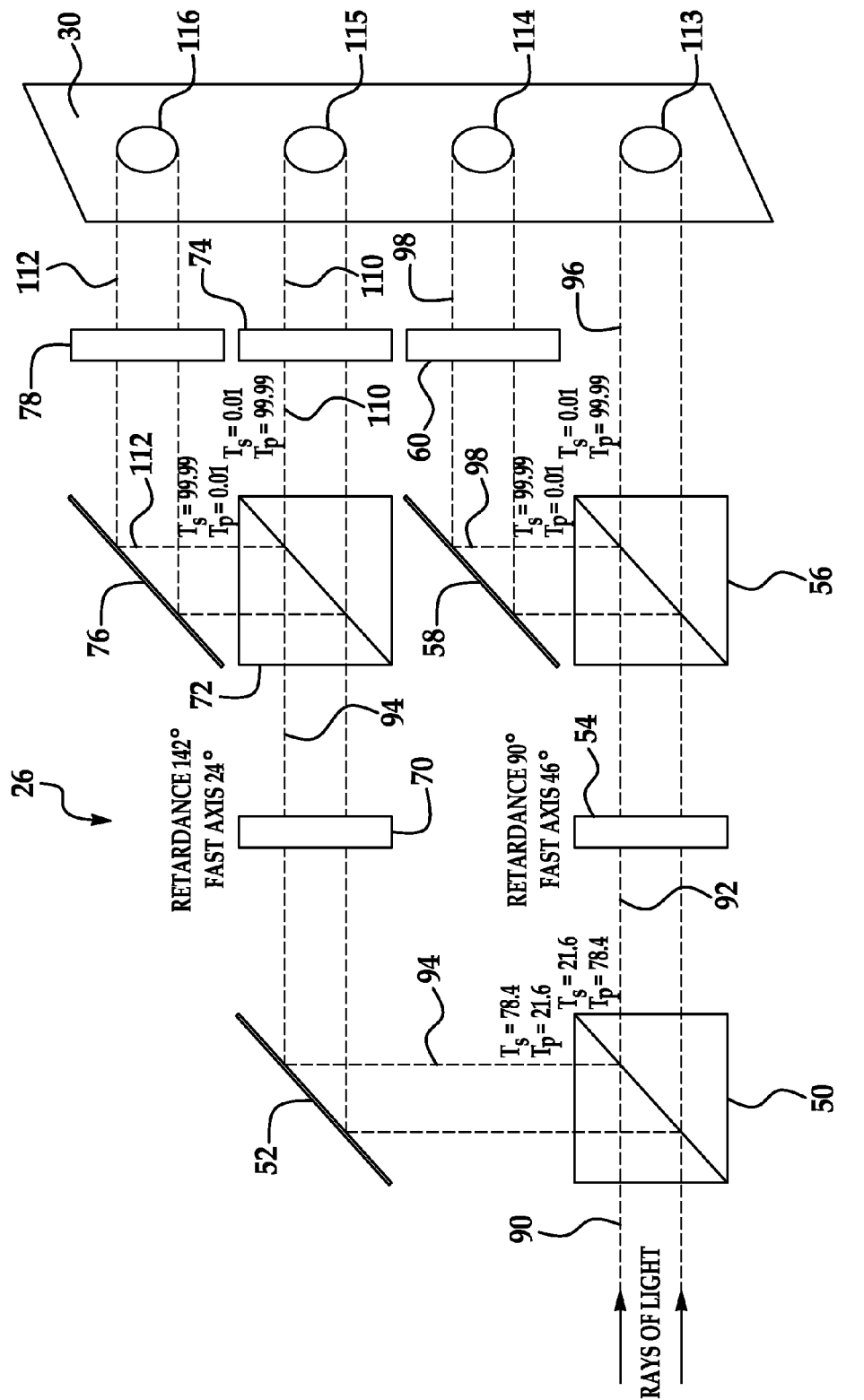

IMAGING POLARIMETER

CROSS-REFERENCE TO RELATED APPLICATION

This patent application claims priority to U.S. Provisional Patent Application Ser. No. 61/174,842, filed May 1, 2009, entitled "OPTIMAL SIMULTANEOUS STOKES' IMAGING POLARIMETER" and which is incorporated by reference herein in its entirety.

BACKGROUND OF THE INVENTION

Polarimeters have been developed that determine an angle of optical rotation of polarized light passing through a sample of material.

Stokes parameters are a set of values that have been utilized to describe a polarization state of light. In particular, Stokes parameters describe light in terms of total intensity (I), a fractional degree of polarization (p) and shape parameters of a polarization ellipse. However, polarimeters have not utilized a rigid monolithic beam splitter therein that bends light rays onto one focal plane to determine Stokes parameters upon receipt of the light rays in real-time.

Remotely collecting accurate polarimetric data (e.g., all four Stokes' parameters) of an object or a scene presents a design challenge. Methods have been proposed for collecting this data, but these methods frequently result in noisy data, require a large number of lenses adding bulk and aberration complexities, and are difficult to register. These drawbacks make remote sensing less accurate and more difficult.

Accordingly, it is desirable to have an improved imaging polarimeter that utilizes a monolithic beam splitter that eliminates the foregoing problems.

SUMMARY OF THE INVENTION

An imaging polarimeter including a monolithic beam splitter configured to receive a first light ray and to split the first light ray into second, third, fourth, and fifth light rays such that the second, third, fourth, and fifth light rays are simultaneously received on a flat focal plane is provided. The imaging polarimeter includes a sensor array disposed on the flat focal plane configured to output first, second, third, and fourth signals indicative of first, second, third and fourth intensities, respectively, of the second, third, fourth, and fifth light rays, respectively. The imaging polarimeter further includes a computer operably coupled to the sensor array. The computer is configured to determine first, second, third, and fourth Stokes parameters for a pixel of the sensor array based on the first, second, third, and fourth signals, respectively. The computer is further configured to store the first, second, third and fourth Stokes parameters in a memory device.

A method of utilizing an imaging polarimeter is provided. The method includes receiving a first light ray at a monolithic beam splitter and splitting the first light ray into second, third, fourth, and fifth light rays utilizing the monolithic beam splitter such that the second, third, fourth, and fifth light rays are simultaneously received on a flat focal plane. The method further includes outputting first, second, third, and fourth signals indicative of first, second, third, and fourth intensities, respectively, of the second, third, fourth, and fifth light rays, respectively, utilizing a sensor array disposed on the focal plane. The method further includes determining first, second, third, and fourth Stokes parameters for a pixel of the sensor array based on the first, second, third, and fourth signals, respectively, utilizing a computer operably coupled to the sensor array. The method further includes storing the first, second, third and fourth Stokes parameters in a memory device utilizing the computer.

An imaging polarimeter including a transparent plate having retical cross-hairs disposed thereon such that light rays propagate through the transparent plate is provided. The imaging polarimeter further includes a monolithic beam splitter configured to split the light rays from the transparent plate such that first, second, third, and fourth images having first, second, third and fourth retical cross-hair regions, respectively, thereon that are received on a flat focal plane. The imaging polarimeter further includes a sensor array disposed on the focal plane configured to generate signals representing the first, second, third and fourth sub-images. The imaging polarimeter further includes a computer operably coupled to the sensor array. The computer is configured to determine a first registration transformation for registering the first and second sub-images with respect to one another utilizing the first and second retical cross-hair regions. The computer is further configured to store the first registration transformation in a memory device.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

FIG. 3 is a simplified schematic of a monolithic beam splitter utilized in the imaging polarimeter of FIG. 1;

DETAILED DESCRIPTION

Figure 1:
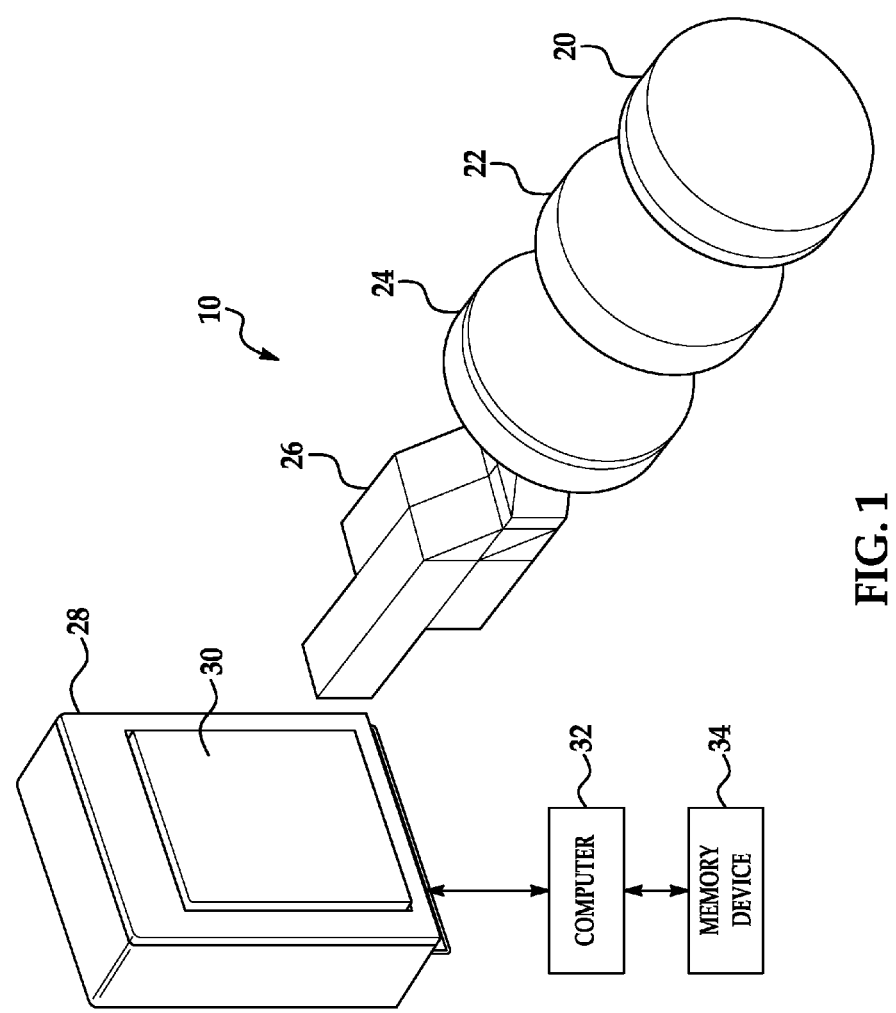
FIG. 1 is an isometric view of an imaging polarimeter in accordance with the present invention.
Figure 2:
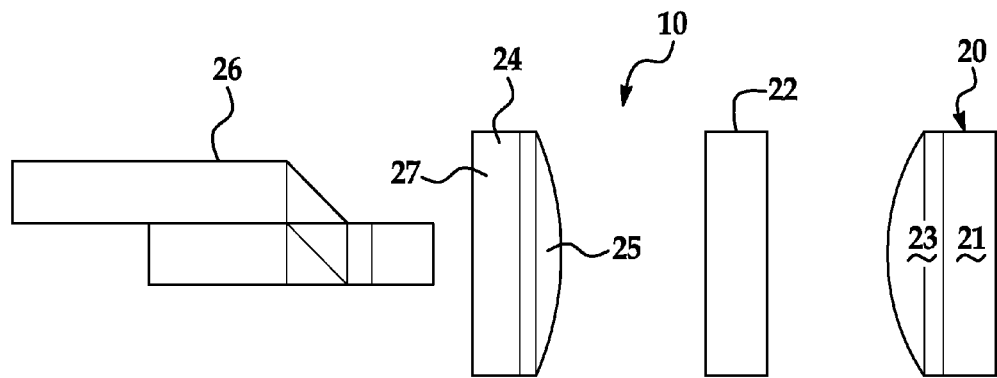
FIG. 2 is a side view of a portion of the imaging polarimeter of FIG. 1.

Referring now to FIGS. 1 and 2, an imaging polarimeter 10 in accordance with an exemplary embodiment is illustrated. The imaging polarimeter 10 includes a collimating lens 20, a bandpass spectral filter 22, a focusing lens 24, a monolithic beam splitter 26, a sensor array 28, a focal plane 30, a computer 32, and a memory device 34. The imaging polarimeter 10 of the invention determines Stokes parameters in real-time for received light. For purposes of this invention, the term real-time means 0.01 seconds or less. Further, the term sub-image means an image of an object formed by light rays traversing through a distinct optical path in a beam splitter on a focal plane. In one non-limiting embodiment, the imaging polarimeter 10 has a compact size less than or equal to 90 cubic inches. This allows the polarimeter 10 to be utilized in numerous applications requiring a compact package size.

The collimating lens 20 is provided to receive light rays from an object and to collimate the light rays propagating through the collimating lens 20. In a non-limiting embodiment, shown in FIG. 2, the collimating lens 20 is a doublet lens and has lens portions 21 and 23. The lens portions 21 and 23 are coupled together and allow broad-band light to pass therethrough. Further, the lens portion 21 may be constructed of a material identified by Product No. SFL6 which is manufactured by Schott North America, Inc., and the lens portion 23 may be constructed of a material identified by Product No. LAKN22 which is manufactured by Schott North America, Inc. In alternative embodiments, the collimating lens 20 can be constructed of different materials than the above listed materials depending on the desired wavelengths of light rays to be collimated.

The bandpass spectral filter 22 is provided to receive light rays from the collimating lens 20 and to output light rays within a wavelength range. In one non-limiting embodiment, bandpass spectral filter 22 may be constructed of fused silica. Further, in one exemplary embodiment, the bandpass spectral filter 22 is constructed to allow light rays in a wavelength range of 1530 nanometers (nm) to 1570 nm to pass therethrough. In an alternative embodiment, the bandpass spectral filter 22 can be constructed to allow light rays in a wavelength range of 628 nm to 638 nm to pass therethrough.

The focusing lens 24 is provided to receive light rays from bandpass spectral filter 22 and to focus the light rays. In the exemplary embodiment shown in FIG. 2, the focusing lens 24 is a doublet lens and has lens portions 25 and 27. The lens portions 25 and 27 are coupled together and allow light to pass therethrough. The lens portion 25 is constructed of a material identified by Product No. BAFN10 which is manufactured by Schott North America, Inc., and the lens portion 27 is constructed of a material identified by Product No. SFL6 which is manufactured by Schott North America, Inc. In alternative embodiments, the focusing lens 24 can be constructed of different materials than the above listed materials depending on the desired wavelengths of light rays to be focused.

The monolithic beam splitter 26 is configured receive light rays from the focusing lens 24 and to split each light ray into four light rays such that the four light rays are simultaneously received on the flat focal plane 30. Each corresponding set of four light rays are utilized to determine four Stokes parameters associated with each corresponding pixel of the sensor array 28.

Figure 4:
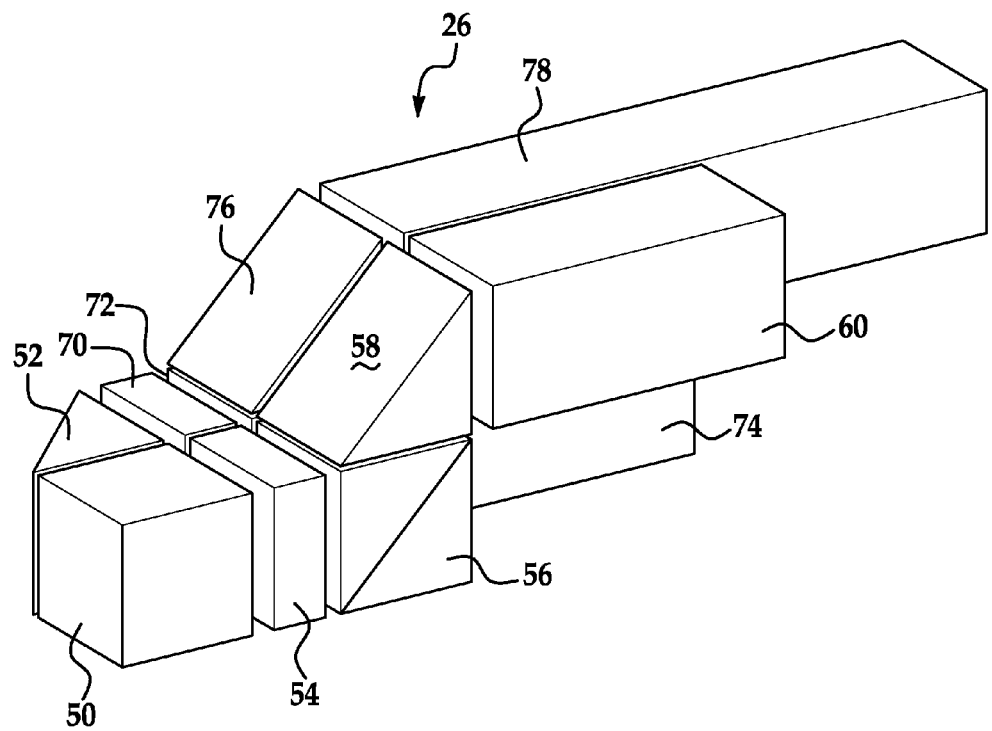
FIG. 4 is an exploded schematic of the monolithic beam splitter utilized in the imaging polarimeter of FIG. 1.

Referring to FIGS. 3 and 4, the monolithic beam splitter 26 includes a partial polarizing beam splitter 50, a prism 52, a wave plate 54, a polarizing beam splitter 56, a prism 58, a focusing compensating block 60, a wave plate 70, a polarizing beam splitter 72, a focusing compensating block 74, a prism 76, and a focusing compensating block 78. It should be noted that the focusing compensating blocks 60, 74 and 78, in the embodiment shown, are non-polarizing and are utilized to equalize the four light ray optical path lengths.

The partial polarizing beam splitter 50 is configured to receive light rays from the focusing lens 24 and to split each received light ray into two light rays. For example, the partial polarizing beam splitter 50 can receive the light ray 90 and split the light ray 90 into light rays 92 and 94. In an embodiment, the polarizing beam splitter 50 is constructed of fused-silica. Further, in the embodiment shown in FIG. 3, the partial polarizing beam splitter 50 has a polarizing beam splitter ratio for s-polarized light of 78.4/21.6 to obtain improved noise rejection. Of course, in alternative embodiments, the polarizing beam splitter ratio for s-polarized light could be in a range of 78.4/21.6±3%. Still further, in one exemplary embodiment, the partial polarizing beam splitter 50 has a polarizing beam splitter ratio for p-polarized light of 21.6/78.4 to obtain improved noise rejection. Of course, in alternative embodiments, the polarizing beam splitter ratio for p-polarized light could be in a range of 21.6/78.4±3%. The partial polarizing beam splitter 50 is coupled to the prism 52 and the wave plate 54 utilizing a transparent adhesive.

The wave plate 54 is an optical device that alters a polarization state of a light ray traveling through the wave plate 54. The wave plate 54 is operated by shifting a phase between two perpendicular polarization components of a light ray. Wave plate 54 can be formed of a birefringent crystal that is cut so that an extraordinary axis or optic axis is parallel to surfaces of the wave plate 54. Light polarized along this axis travels through the crystal at a different speed than light with the perpendicular polarization, forming a phase difference or phase shift. When the extraordinary index is smaller than the ordinary index, the extraordinary axis is called the fast axis and the perpendicular direction in a plane of the surfaces is called a slow axis.

The wave plate 54 is configured to receive light rays from the partial polarizing beam splitter 50 and to phase shift the light rays a predetermined amount. Further, the wave plate 54 has a fast axis that is rotated another predetermined amount. In one exemplary embodiment shown in FIG. 3, the wave plate 54 phase shifts or retards the received light rays 90 degrees as the light rays propagate through the wave plate 54. Further, the wave plate 54 has a fast axis that is rotated 46 degrees. Of course, in alternative embodiments, the wave plate 54 could phase shift the received light rays in a range of 88-92 degrees. Further, the wave plate 54 could have a fast axis rotated in a range of 44-48 degrees. In one exemplary embodiment, the wave plate 54 is constructed of quartz. The wave plate 54 is coupled to the partial polarizing beam splitter 50, the polarizing beam splitter 56, and the wave plate 70, utilizing a transparent adhesive.

The polarizing beam splitter 56 is configured to receive light rays from the wave plate 54 and to split each received light ray into two light rays. For example, the polarizing beam splitter 56 can receive the light ray 92 and split the light ray 92 into light rays 96, 98. The light ray 96 propagates from the polarizing beam splitter 56 to a first position on the focal plane array 30, and the light ray 98 propagates from the polarizing beam splitter 56 to the prism 58. In an embodiment, the polarizing beam splitter 56 is constructed of fused-silica. Further, in the embodiment shown in FIG. 3, the polarizing beam splitter 56 has a polarizing beam splitter ratio for s-polarized light of 99.99/0.01. Of course, in alternative embodiments, the polarizing beam splitter ratio for s-polarized light could be in a range of 99.99/0.01±3%. The polarizing beam splitter 56 has a polarizing beam splitter ratio for p-polarized light of the inverse of the s-polarized light, i.e., 0.01/99.99. Of course, in alternative embodiments, the polarizing beam splitter ratio for p-polarized light could in a range of 0.01/99.99±3%. The polarizing beam splitter 56 is coupled to the wave plate 54 and the prism 58 utilizing a transparent adhesive.

The prism 58 is configured to receive light rays from the polarizing beam splitter 56 and to reflect the light rays through the focusing compensating block 60 to the focal plane 30. For example, the prism 58 receives the light ray 98 from the polarizing beam splitter 56 and reflects the light ray 98 through the focusing compensating block 60 to the focal plane 30. In a non-limiting embodiment, the prism 58 is constructed of fused-silica. The prism 58 is coupled to the polarizing beam splitter 56 and the focusing compensating block 60 utilizing a transparent adhesive.

The focusing compensating block 60 is provided to focus received light rays from the prism 58 onto the focal plane 30. For example, the focusing compensating block 60 focuses the received light ray 98 on the focal plane 30. In one exemplary embodiment, the focusing compensating block 60 is constructed of fused-silica. The focusing compensating block 60 is coupled to the prism 58 and the focusing compensating block 78 utilizing a transparent adhesive.

The prism 52 is configured to receive light rays from the partial polarizing beam splitter 50 and to bend the light rays a first predetermined amount. In the embodiment shown, the prism 50 bends the received light rays 90 degrees as the light rays propagate through the prism 50. For example, the prism 50 bends the received light ray 90, 90 degrees, as the light ray 90 propagates through the prism 50. Of course, in alternative embodiments, the beam splitter 50 could bend the received light ray 90 within a range of 88-92 degrees. In one exemplary embodiment, the prism 52 is a total internal reflectance prism and is constructed of fused-silica. The prism 52 is coupled to the partial polarizing beam splitter 50 and the wave plate 70 utilizing a transparent adhesive. It should be noted that the prism 52 is utilized to bend received light rays to a direction parallel to light rays received by the partial polarizing beam splitter 50 so that all of the light rays being output by the imaging polarimeter 10 can be received on one flat focal plane 30.

The wave plate 70 is configured to receive light rays from the prism 52 and to phase shift the light rays a predetermined amount. Further, the wave plate 70 has a fast axis that is rotated another predetermined amount. In the exemplary embodiment shown, the wave plate 70 phase shifts or retards the received light rays, 142 degrees, as the light rays propagate through the wave plate 70. Further, the wave plate 70 has a fast axis that is rotated 24 degrees. Of course, in alternative embodiments, the wave plate 70 could phase shift the received light rays within a range of 140-144 degrees. Further, the wave plate 70 could have a fast axis rotated within a range of 22-26 degrees. In an exemplary embodiment, the wave plate 70 is constructed of quartz. The wave plate 70 is coupled to the prism 52, the wave plate 54, and the polarizing beam splitter 72 utilizing a transparent adhesive.

The polarizing beam splitter 72 is configured to receive light rays from the wave plate 70 and to split each received light ray into two light rays. For example, the polarizing beam splitter 72 can receive the light ray 94 and split the light ray 94 into light rays 110, 112. The light ray 110 propagates from the polarizing beam splitter 72 through the focusing compensating block 74 to a third position on the focal plane array 30. The light ray 112 propagates from the polarizing beam splitter 72 to the prism 76. In an exemplary embodiment, the polarizing beam splitter 72 is constructed of fused-silica. The polarizing beam splitter 72 of FIG. 3 has a polarizing beam splitter ratio for s-polarized light of 99.99/0.01. Of course, in alternative embodiments, the polarizing beam splitter ratio for s-polarized light could be in a range of 99.99/0.01±3%. The polarizing beam splitter 72 has a polarizing beam splitter ratio for p-polarized light of 0.01/99.99 which is the inverse of the s-polarized light. Of course, in alternative embodiments, the polarizing beam splitter ratio for p-polarized light could be in a range of 0.01/99.99±3%. The polarizing beam splitter 72 is coupled to the wave plate 70, the polarizing beam splitter 56, the prism 76, and the polarizing beam splitter 56 utilizing a transparent adhesive.

The focusing compensating block 74 is provided to focus received light rays from the polarizing beam splitter 72 onto the focal plane 30. For example, the focusing compensating block 74 focuses the received light ray 110 on the focal plane 30. In the exemplary embodiment, the focusing compensating block 74 is constructed of fused-silica. The focusing compensating block 74 is coupled to the polarizing beam splitter 72 and the focusing compensating block 78 utilizing a transparent adhesive.

The prism 76 is configured to receive light rays from the polarizing beam splitter 72 and to reflect the light rays through the focusing compensating block 78 to the focal plane 30. For example, the prism 76 receives the light ray 112 from the polarizing beam splitter 72 and reflects the light ray 112 through the focusing compensating block 78 to the focal plane 30. In the embodiment shown, the prism 76 is constructed of fused-silica. The prism 76 is coupled to the polarizing beam splitter 72, the prism 58, and the focusing compensating block 78 utilizing a transparent adhesive.

The focusing compensating block 78 is provided to focus received light rays from the prism 76 onto the focal plane 30. For example, the focusing compensating block 78 focuses the received light ray 112 on the focal plane 30. In the exemplary embodiment shown, the focusing compensating block 78 is constructed of fused-silica. The focusing compensating block 78 is coupled to the prism 76 and the focusing compensating block 60 utilizing a transparent adhesive.

Referring to FIGS. 1 and 3, the sensor array 28 is configured to receive light rays from the monolithic beam splitter 26 and to generate signals indicative of intensities of the received light rays. The sensor array 28 is disposed at the focal plane 30. The sensor array 28 has a plurality of pixel elements that each generate a signal indicative of an intensity of the light ray contacting the pixel element. In particular, the sensor array 28 can receive light rays corresponding to four sub-images, for example the sub-images 113, 114, 115, 116 which are indicative of light spectra being emitted from an object. As shown, the sensor array 28 is electrically coupled to the computer 32.

The computer 32 is operably coupled to the sensor array 28 and to the memory device 34. The computer 32 is configured to receive signals from the sensor array 28 indicative of intensities of received light rays. Further, the computer 32 is configured to calculate in real time four Stokes parameters for each pixel of the sensor array 28 based upon corresponding light rays received on the focal plane 30 and the sensor array 28 in real-time. In particular, the focal plane normalized intensity (I) at each pixel is represented by the following equation.

$$I = WS \tag{1}$$

where: S represents Stokes parameters of a scene and is 4×1 matrix; and W represents a measurement matrix that corresponds to the physical characteristics of the monolithic beam splitter and is a 4×4 matrix.

A more detailed explanation of the measurement matrix W will now be provided. The measurement matrix W has a Mueller matrix for each optical path. The below equations provide the Mueller matrices for each of the four optical paths.

$$M^1 = M_{rotation}{}^{-90°} M_{PBS}{}^T M_{rotation}{}^{+90°} M_{WP}{}^1 M_{PPBS}{}^T \tag{2}$$

$$M^2 = M_{rotation}{}^{-90°} M_{PBS}{}^R M_{rotation}{}^{+90°} M_{WP}{}^1 M_{PPBS}{}^T \tag{3}$$

$$M^3 = M_{rotation}{}^{-90°} M_{PBS}{}^T M^{+90°} M_{WP}{}^2 M_{prism} M_{PPBS}{}^R \tag{4}$$

$$M^4 = M_{rotation}{}^{-90°} M_{PBS}{}^R M_{rotation}{}^{+90°} M_{WP}{}^2 M_{prism} M_{PPBS}{}^R \tag{5}$$

Referring to FIG. 3, the matrix $M^1$ corresponds to the optical path associated with the light rays forming the sub-image 116. The matrix $M^2$ corresponds to the optical path associated with the light rays forming the sub-image 115. The matrix $M^3$ corresponds to the optical path associated with the light rays forming the sub-image 113. The matrix $M^4$ corresponds to the optical path associated with the light rays forming the sub-image 114.

Further, $M_{rotation}^{-90°}$ and $M_{rotation}^{+90°}$ are rotation Mueller matrices of minus and plus 90 degrees respectively. $M_{PBS}^{T}$ and $M_{PBS}^{R}$ are the Mueller matrices of a polarizing beam splitter (PBS) in reflection and transmission respectively. $M_{WP}^{1}$ and $M_{WP}^{2}$ are Mueller matrices of a wave plate for the two wave plates. $M_{prism}$ is the Mueller matrix for a total internal reflectance prism at 45 degrees. $M_{PPBS}^{T}$ and $M_{PPBS}^{R}$ are the Mueller matrices for a polarizing beam splitter in reflection and transmission respectively. To obtain the measurement matrix W, the top row of each of the optical paths' Mueller matrix forms the rows of the measurement matrix W as shown below.

$$W = \begin{bmatrix} M^1_{1,1-4} \\ M^2_{1,1-4} \\ M^3_{1,1-4} \\ M^4_{1,1-4} \end{bmatrix} \quad (6)$$

The above measurement matrix W is a 4×4 matrix.

Since the focal plane normalized intensity (I) is known for each pixel of the sensor array 28 from the corresponding signals output by the sensor array 28, the computer 30 calculates four Stokes parameters associated with each pixel of the sensory array 28 utilizing the following equation:

$$S_{est} = W_{est}^{-1} I \quad (7)$$

wherein $W_{est}^{-1}$ represents an inverse of an estimated measurement matrix that corresponds to physical characteristics of the monolithic beam splitter 26 and is a 4×4 matrix; and $S_{est}$ corresponds to estimated Stokes parameters of a scene and is a 4×1 matrix. The computer 32 stores $S_{est}$ in the memory device 34.

Figure 5:
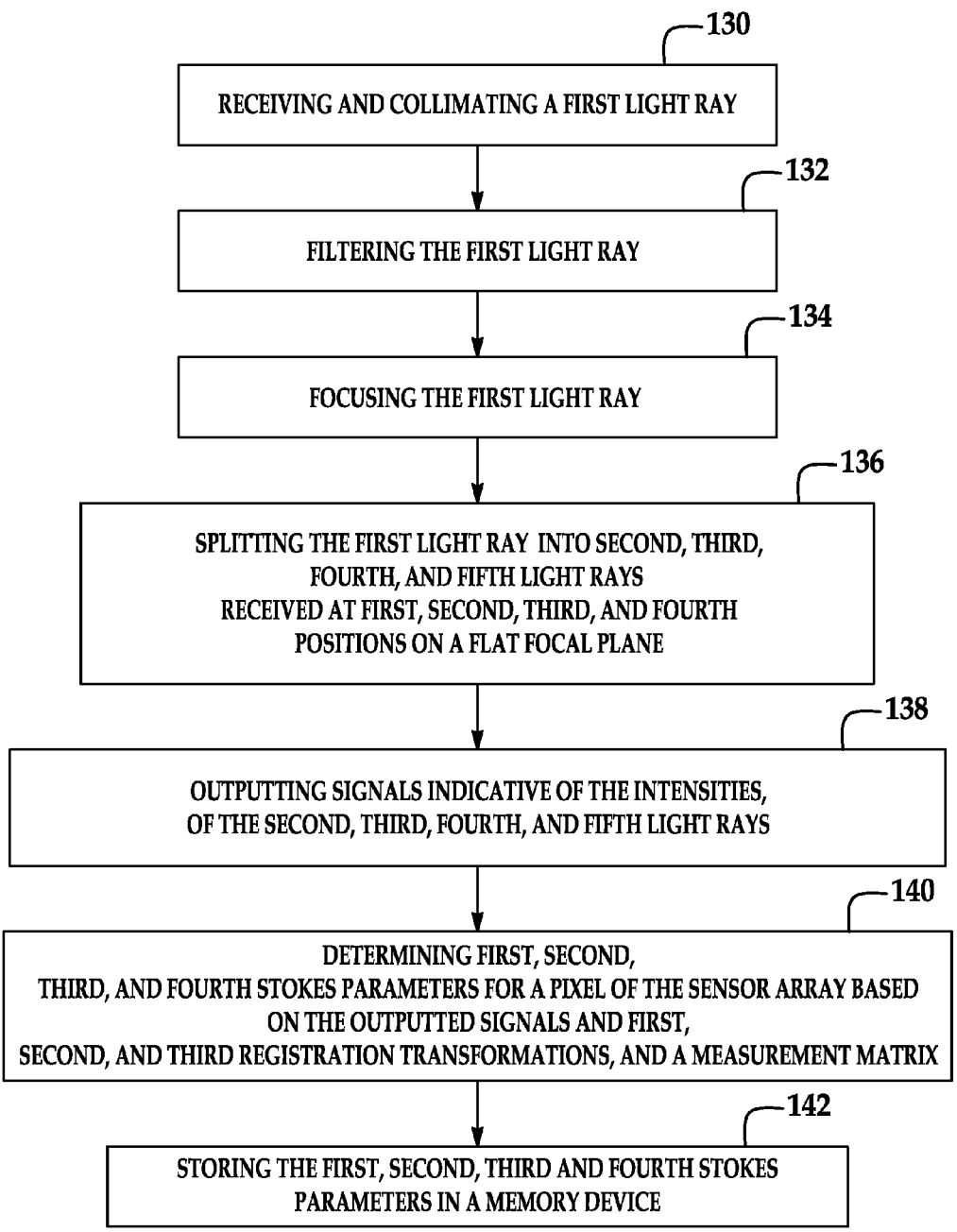
FIGS. 5-6 show a method for utilizing an imaging polarimeter in accordance with one aspect of the invention.
Figure 6:
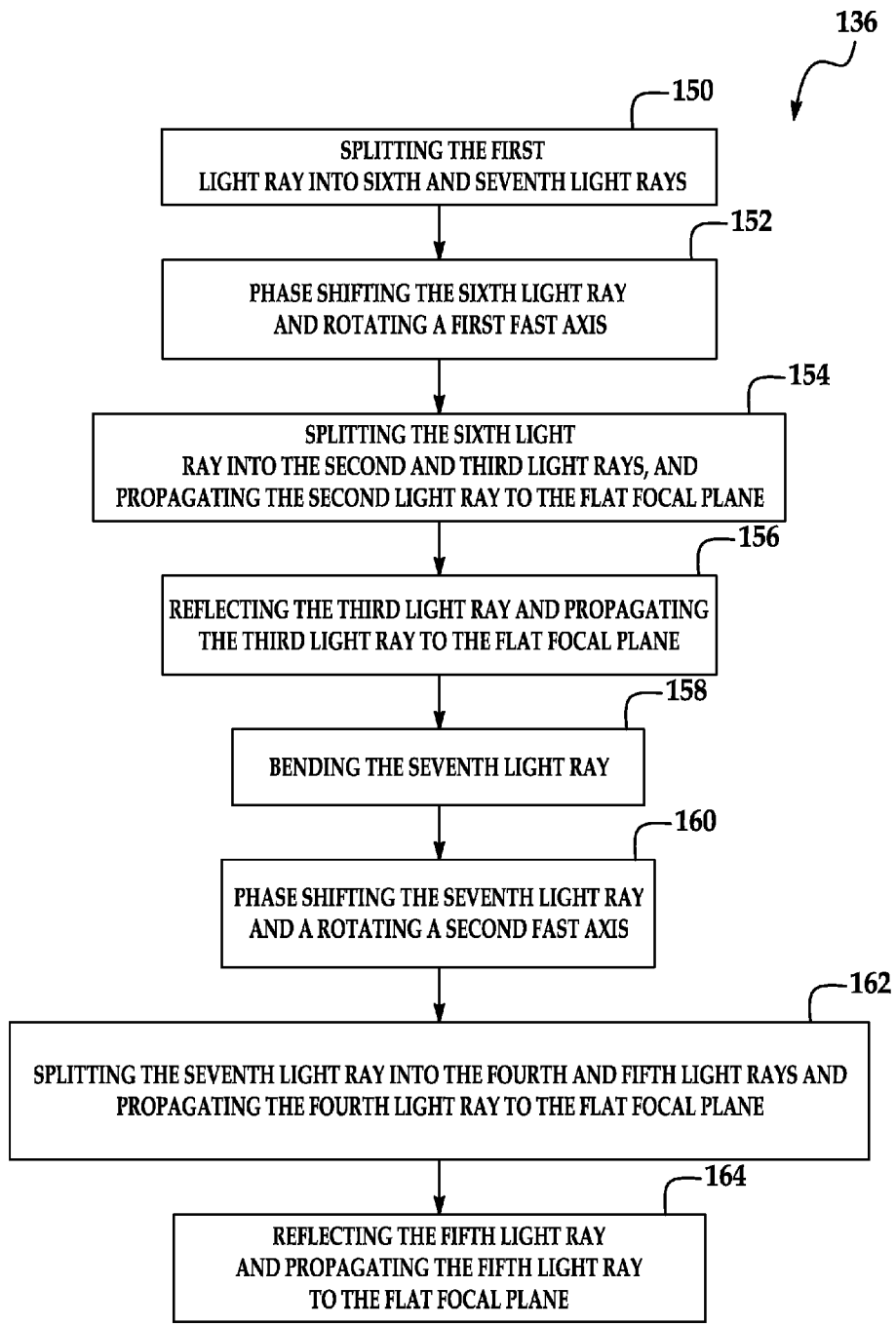

Referring to FIGS. 3, 5 and 6, a method for utilizing the imaging polarimeter 10 in accordance with another exemplary embodiment of the invention is shown and is described herein in detail. Of course, the details of the method shown are only exemplary in nature. Variations and alterations to the method may be implemented by one skilled in the art.

At step 130, the collimating lens 20 receives at least a first light ray and collimates the first light ray.

At step 132, the bandpass spectral filter 22 receives the first light ray from the collimating lens 20 and outputs the first light ray within a predetermined wavelength range.

At step 134, the focusing lens 24 receives the first light ray from the bandpass spectral filter 22 and focuses the first light ray therefrom.

At step 136, the monolithic beam splitter 26 receives the first light ray from the focusing lens 24 and splits the first light ray from the focusing lens into second, third, fourth, and fifth light rays such that the second, third, fourth, and fifth light rays are simultaneously received at first, second, third and fourth positions, respectively, on the flat focal plane 30.

At step 138, the sensor array 28 disposed on the flat focal plane 30 outputs first, second, third, and fourth signals indicative of first, second, third, and fourth intensities, respectively, of the second, third, fourth, and fifth light rays, respectively.

At step 140, the computer 32 operably coupled to the sensor array 28 determines first, second, third, and fourth Stokes parameters for a pixel of the sensor array 28 based on the first, second, third, and fourth signals, respectively, and first, second, and third registration transformations, and a measurement matrix. As used herein, a registration transformation is a mathematical algorithm for translating, rotating and scaling sub-images that are associated with a portion of a scene of an object to associated similar pixels in the sub-images. In one exemplary embodiment contemplated by the invention, each respective registration transformation is determined for two respective sub-images for translating, rotating, and scaling two sub-images that are associated with a portion of a scene of an object. The first registration transformation is utilized to associate a pixel on the sensor array 30 receiving the third light ray with a pixel receiving the second light ray. The second registration transformation is utilized to associate the pixel on the sensor array 30 receiving the fourth light ray with the pixel receiving the second light ray. The third registration transformation is utilized to associate a pixel on the sensor array 30 receiving the fifth light ray with the pixel receiving the second light ray. After the pixels are registered with one another and the Focal Plane Normalized Intensity (I) is obtained for each pixel, the measurement matrix W is utilized to determine the Stokes parameters as discussed above with respect to Equation 7.

At step 142, the computer 32 stores the first, second, third and fourth Stokes parameters in the memory device 34.

Referring again to step 136, the substeps 150-164 for performing the step 136 will now be explained.

At step 150, the partial polarizing beam splitter 50 receives the first light ray from the focusing lens 24 and splits the first light ray into sixth and seventh light rays.

At step 152, the wave plate 54 receives the sixth light ray from the polarizing beam splitter 50 and phase shifts the sixth light ray a first predetermined amount. The wave plate 54 has a first fast axis that is rotated a second predetermined amount.

At step 154, the polarizing beam splitter 56 receives the sixth light ray from the wave plate 54 and splits the sixth light ray into the second and third light rays. The second light ray propagates from the polarizing beam splitter 56 to the flat focal plane 30.

At step 156, the prism 58 receives the third light ray from the polarizing beam splitter 56 and reflects the third light ray such that the third light ray propagates from the prism 58 through the focusing compensating block 60 to the flat focal plane 30.

At step 158, the prism 52 receives the seventh light ray from the partial polarizing beam splitter 50 and bends the seventh light ray a third predetermined amount.

At step 160, the wave plate 70 receives the seventh light ray from the prism 52 and phase shifts the seventh light ray a fourth predetermined amount. The wave plate 70 has a second fast axis that is rotated a fifth predetermined amount.

At step 162, the polarizing beam splitter 72 receives the seventh light ray from the wave plate 70 and splits the seventh light ray into the fourth and fifth light rays. The fourth light ray propagates from the polarizing beam splitter 72 through the focusing compensating block 74 to the flat focal plane 30.

At step 164, the prism 76 receives the fifth light ray from the polarizing beam splitter 72 and reflects the fifth light ray from the prism 76 such that the fifth light ray propagates from the prism 76 through the focusing compensating block 78 to the flat focal plane 30.

Figure 7:
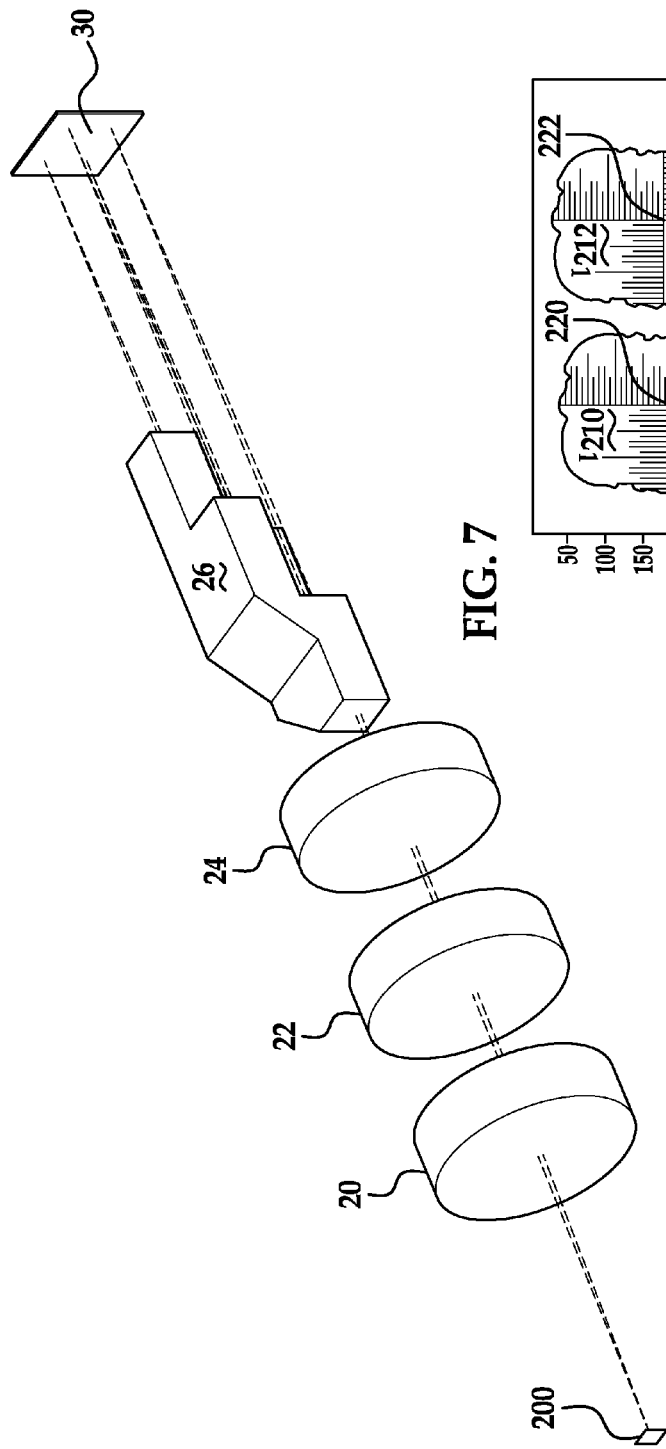
FIG. 7 is an isometric view of the imaging polarimeter of FIG. 1 showing another aspect of the invention.

Referring to FIGS. 3 and 7, the calibration of the imaging polarimeter 10 to obtain accurate registration of the individual images is shown. It should be noted that a registration error could lead to significant Stokes estimation errors. Accordingly, the imaging polarimeter 10 is calibrated to obtain a precise registration of the four different sub-images on the focal plane array 30. During registration, registration transformations are determined for transforming coordinates from a sub-image to another sub-image. After calibration is completed, the registration transformations are utilized to register sub-images to obtain Stokes parameters in real-time, which eliminates a need for search-type algorithms to be executed for each subsequent sub-image.

Figure 9:
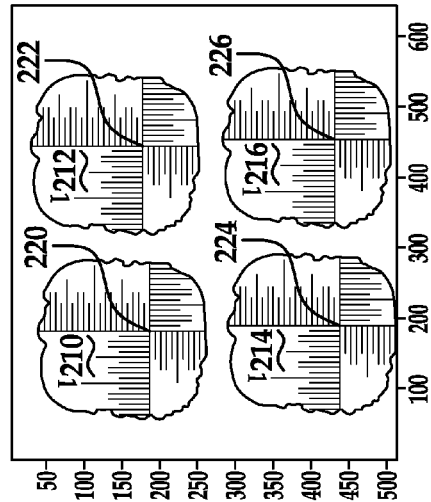
FIG. 9 is a detailed schematic of yet another aspect of the invention shown in FIG. 7.
Figure 8:
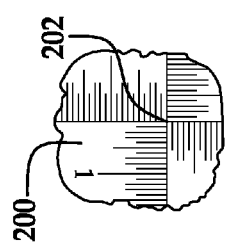
FIG. 8 is a detailed schematic of a portion of FIG. 7.

Referring to FIGS. 8 and 9, to reduce the error in the Stokes estimation, an accurate registration of the sub-images 210, 212, 214 and 216 is performed. In particular, a transparent plate 200 with reticule cross-hairs 202 is inserted at an intermediate image plane such that unpolarized light rays from an object pass through the transparent plate 200 to the collimating lens 20. The light rays corresponding to the original image or scene of the object is utilized to generate the sub-images 210, 212, 214 and 216 output by the monolithic beam splitter 26 onto the focal plane 30. The sub-images 210, 212, 214 have reticule cross-hair regions 220, 222, 224, 226, respectively, of about equal intensities. These sub-images can be registered accurately by generating registration transformations for associating pixels from one sub-image to another. It should be noted that the transparent plate 200 is removed prior to data acquisition for obtaining Stokes parameters. In other words, the transparent plate 200 is typically only utilized for initial calibration of the imaging polarimeter to obtain the registration transformations.

Figure 10:
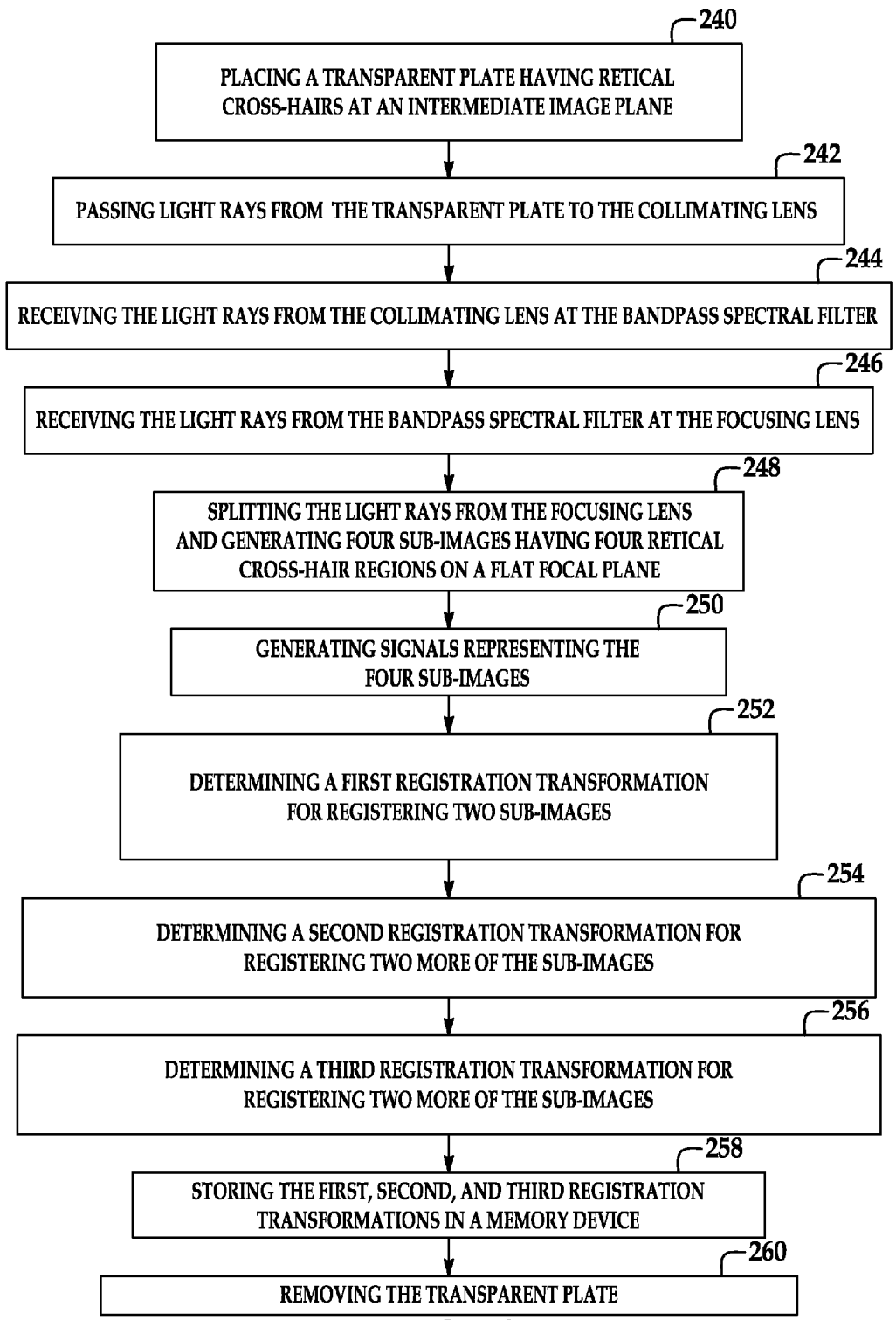
FIG. 10 shows a method a method for calibrating the imaging polarimeter of FIG. 7.

Referring to FIG. 10, a method for calibrating the imaging polarimeter 10 utilizing the transparent plate 200 is shown.

At step 240, the transparent plate 200 is disposed at an intermediate image plane. The transparent plate 200 has retical cross-hairs 202 disposed thereon and has light rays propagating therethrough.

At step 242, the collimating lens 20 receives light rays from transparent plate 200 and collimates the light rays.

At step 244, the bandpass spectral filter 22 receives the light rays from the collimating lens 20 and outputs light rays within a predetermined wavelength range.

At step 246, the focusing lens 24 receives the light rays from the bandpass spectral filter 22 and focuses the light rays therefrom.

At step 248, the monolithic beam splitter 26 splits the light rays from the focusing lens 24 such that sub-images 210, 212, 214 and 216 having retical cross-hair regions 220, 222, 224 and 226, respectively, thereon that are received on the flat focal plane 30.

At step 250, the sensor array 28 disposed on the focal plane 30 generates signals representing the sub-images 210, 212, 214 and 216.

At step 252, the computer 32 operably coupled to the sensor array 28 determines a first registration transformation utilizing a registration algorithm and the retical cross-hair regions 220 and 222 for registering the sub-images 210 and 212 with respect to one another.

At step 254, the computer 32 determines a second registration transformation utilizing the registration algorithm and the retical cross-hair regions 220 and 224 for registering the images 210 and 214 with respect to one another.

At step 256, the computer 32 determines a third registration transformation utilizing the registration algorithm and the retical cross-hair regions 220 and 226 for registering the images 210 and 216 with respect to one another.

At step 258, the computer 32 stores the first, second, and third registration transformations in the memory device 34.

At step 260, the transparent plate 200 is removed from the intermediate image plane.

The imaging polarimeter 10 provides substantial advantages over other polarimeters. In particular, the imaging polarimeter 10 utilizes a rigid monolithic beam splitter such that light rays can be simultaneously received on a flat focal plane to determine Stokes parameters in real-time for received light. Further, the imaging polarimeter 10 has the ability to be manufactured in a compact size less than or equal to 90 cubic inches that is extremely useful for telescopic applications.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

Having thus described the invention, it is claimed:

1. An imaging polarimeter, comprising:
a monolithic beam splitter configured to receive a first light ray and to split the first light ray into second, third, fourth, and fifth light rays such that the second, third, fourth, and fifth light rays are simultaneously received on a flat focal plane;
a sensor array disposed on the flat focal plane configured to output first, second, third, and fourth signals indicative of first, second, third and fourth intensities, respectively, of the second, third, fourth, and fifth light rays, respectively; and
a computer operably coupled to the sensor array, the computer configured to determine first, second, third, and fourth Stokes parameters for a pixel of the sensor array based on the first, second, third, and fourth signals, respectively, the computer further configured to store the first, second, third and fourth Stokes parameters in a memory device.

2. The imaging polarimeter of claim 1, wherein the second, third, fourth, and fifth light rays are simultaneously received at first, second, third, and fourth locations, respectively, on the flat focal plane.

3. The imaging polarimeter of claim 1, further comprising:
a collimating lens configured to receive at least the first light ray and to collimate the first light ray;
a bandpass spectral filter configured to receive the first light ray from the collimating lens and to output the first light ray within a predetermined frequency band; and
a focusing lens configured to receive the first light ray from the bandpass spectral filter and to focus the first light ray therefrom onto the monolithic beam splitter.

4. The imaging polarimeter of claim 1, wherein the monolithic beam splitter comprises:
a first polarizing beam splitter configured to receive the first light ray and to split the first light ray into sixth and seventh light rays;
a first wave plate configured to receive the sixth light ray from the first polarizing beam splitter and to phase shift the sixth light ray a first predetermined amount, the first wave plate having a first fast axis that is rotated a second predetermined amount; and
a second polarizing beam splitter configured to receive the sixth light ray from the first wave plate and to split the sixth light ray into the second and third light rays, the second light ray propagating from the second polarizing beam splitter to the flat focal plane.

5. The imaging polarimeter of claim 4, wherein the first predetermined amount is in a range of 88 to 92 degrees.

6. The imaging polarimeter of claim 4, wherein the second predetermined amount is in a range of 44 to 48 degrees.

7. The imaging polarimeter of claim 4, wherein the monolithic beam splitter further comprises a first prism configured to receive the third light ray from the second polarizing beam splitter and to reflect the third light ray such that the third light ray propagates from the first prism through a first focusing compensating block to the flat focal plane.

8. The imaging polarimeter of claim 7, wherein the monolithic beam splitter further comprises:
   a second prism configured to receive the seventh light ray from the first polarizing beam splitter and to bend the seventh light ray a third predetermined amount;
   a second wave plate configured to receive the seventh light ray from the second prism and to phase shift the seventh light ray a fourth predetermined amount, the second wave plate having a second fast axis that is rotated a fifth predetermined amount; and
   a third polarizing beam splitter configured to receive the seventh light ray from the second wave plate and to split the seventh light ray into the fourth and fifth light rays, the fourth light ray propagating from the third polarizing beam splitter through a second focusing compensating block to the flat focal plane.

9. The imaging polarimeter of claim 8, wherein the fourth predetermined amount is in a range of 140 to 144 degrees.

10. The imaging polarimeter of claim 8, wherein the fifth predetermined amount is in a range of 22 to 26 degrees.

11. The imaging polarimeter of claim 8, wherein the monolithic beam splitter further comprises a third prism configured to receive the fifth light ray from the third polarizing beam splitter and to reflect the fifth light ray from the third prism such that the fifth light ray propagates from the third prism through a third focusing compensating block to the flat focal plane.

12. The imaging polarimeter of claim 1, wherein the imaging polarimeter has a volume less than or equal to 90 cubic inches.

13. A method of utilizing an imaging polarimeter, the imaging polarimeter including a monolithic beam splitter, a flat focal plane, a sensor array, a computer and a memory device, the method comprising:
   receiving a first light ray at the monolithic beam splitter and splitting the first light ray into second, third, fourth, and fifth light rays utilizing the monolithic beam splitter such that the second, third, fourth, and fifth light rays are simultaneously received on the flat focal plane;
   outputting first, second, third, and fourth signals indicative of first, second, third, and fourth intensities, respectively, of the second, third, fourth, and fifth light rays, respectively, utilizing the sensor array disposed on the focal plane;
   determining first, second, third, and fourth Stokes parameters for a pixel of the sensor array based on the first, second, third, and fourth signals, respectively, utilizing a computer operably coupled to the sensor array; and
   storing the first, second, third and fourth Stokes parameters in the memory device utilizing the computer.

14. The method of claim 13, wherein the imaging polarimeter further includes a collimating lens, a bandpass spectral filter, a focusing lens, the method further comprising:
   receiving at least the first light ray at the collimating lens and collimating the first light ray utilizing the collimating lens;
   receiving the first light ray from the collimating lens at the bandpass spectral filter and outputting the first light ray within a predetermined wavelength range utilizing the bandpass spectral filter; and
   receiving the first light ray from the bandpass spectral filter at the focusing lens and focusing the first light ray from the bandpass spectral filter onto the monolithic beam splitter utilizing the focusing lens.

15. The method of claim 13, wherein the second, third, fourth, and fifth light rays are simultaneously received at first, second, third, and fourth locations, respectively, on the flat focal plane.

16. The method of claim 13, wherein splitting the first light ray at the monolithic beam splitter, comprises:
   receiving the first light ray at a first polarizing beam splitter and splitting the first light ray into sixth and seventh light rays utilizing the first polarizing beam splitter;
   receiving the sixth light ray from the first polarizing beam splitter at a first wave plate and phase shifting the sixth light ray a first predetermined amount, the first wave plate having a first fast axis that is rotated a second predetermined amount; and
   receiving the sixth light ray from the first wave plate at a second polarizing beam splitter and splitting the sixth light ray into the second and third light rays utilizing the second polarizing beam splitter, the second light ray propagating from the second polarizing beam splitter to the flat focal plane.

17. The method of claim 16, wherein the first predetermined amount is in a range of 88 to 92 degrees.

18. The method of claim 16, wherein the second predetermined amount is in a range of 44 to 48 degrees.

19. The method of claim 16, further comprising receiving the third light ray from the second polarizing beam splitter at a first prism and reflecting the third light ray from the first prism such that the third light ray propagates from the first prism through a first focusing compensating block to the flat focal plane.

20. The method of claim 19, further comprising:
   receiving the seventh light ray from the first polarizing beam splitter at a second prism and bending the seventh light ray a third predetermined amount utilizing the second prism;
   receiving the seventh light ray from the second prism at a second wave plate and phase shifting the seventh light ray a fourth predetermined amount, the second wave plate having a second fast axis that is rotated a fifth predetermined amount; and
   receiving the seventh light ray from the second wave plate at a third polarizing beam splitter and splitting the seventh light ray into the fourth and fifth light rays utilizing the third polarizing beam splitter, the fourth light ray propagating from the third polarizing beam splitter through a second focusing compensating block to the flat focal plane.

21. The method of claim 20, further comprising receiving the fifth light ray from the third polarizing beam splitter at a third prism and reflecting the fifth light ray from the third prism such that the fifth light ray propagates from the third prism through a third focusing compensating block to the flat focal plane.

22. An imaging polarimeter, comprising:
   a transparent plate having retical cross-hairs disposed thereon, light rays propagating through the transparent plate;
   a monolithic beam splitter configured to split the light rays from the transparent plate such that first, second, third, and fourth images having first, second, third and fourth retical cross-hair regions, respectively, thereon that are received on a flat focal plane;

a sensor array disposed on the focal plane configured to generate signals representing the first, second, third and fourth sub-images; and a computer operably coupled to the sensor array, the computer configured to determine a first registration transformation for registering the first and second sub-images with respect to one another utilizing the first and second retical cross-hair regions, the computer further configured to store the first registration transformation in a memory device.

23. The imaging polarimeter of claim 22, wherein the computer is further configured to determine a second registration transformation for registering the first and third sub-images with respect to one another utilizing the first and third retical cross-hair regions, the computer further configured to store the second registration transformation in the memory device.

24. The imaging polarimeter of claim 23, wherein the computer is further configured to determine a third registration transformation for registering the first and fourth sub-images with respect to one another utilizing the first and fourth retical cross-hair regions, the computer further configured to store the third registration transformation in the memory device.

* * * * *